United States Patent [19]

Magovern et al.

[11] 4,142,531

[45] Mar. 6, 1979

[54] CATHETER

[75] Inventors: George J. Magovern, Pittsburgh; Frederick J. Shipko, Spring Church; George W. Roland, Indiana, all of Pa.

[73] Assignee: Coratomic, Inc., Indiana, Pa.

[21] Appl. No.: 856,681

[22] Filed: Dec. 2, 1977

Related U.S. Application Data

[63] Continuation-in-part of Ser. No. 756,630, Jan. 4, 1977, abandoned.

[51] Int. Cl.² ............................................. A61N 1/04
[52] U.S. Cl. .................................. 128/418; 128/419 P
[58] Field of Search ..................... 128/404, 418, 419 P, 128/2.06 E, DIG. 4

[56] References Cited

U.S. PATENT DOCUMENTS

| | | | |
|---|---|---|---|
| 3,800,784 | 4/1974 | Kiszel et al. | 128/418 |
| 3,835,864 | 9/1974 | Rasor et al. | 128/418 |
| 3,999,555 | 12/1976 | Person | 128/418 |
| 4,011,875 | 3/1977 | Lehr et al. | 128/419 P |

FOREIGN PATENT DOCUMENTS 1575665  6/1969  France .................................. 128/419 P

Primary Examiner—William E. Kamm
Attorney, Agent, or Firm—Hymen Diamond

[57] ABSTRACT

A catheter to be electrically connected to a part of an organ of a body, typically, the muscle of the heart. The catheter includes a hollow electrical conductor having a resilient clamp at the end where it is to be connected. The clamp is manipulated by a manipulator which is removably inserted into the conductor or by a string which is permanently connected to the clamp. The jaws of the clamp are normally maintained closed by a spring. The spring is retracted by the manipulator or string which pulls on a pin connected to the spring permitting the jaws of the jaws to spring open. The open jaws are then positioned near the body part to be engaged and the manipulator or string is manipulated to release the spring so that the jaws are closed in engagement with the body part.

The clamp extends to the conductor through a seal which effectively prevents the penetration of body fluids to the conductor. The surface of the jaws is composed of, or has a coating of, an electrically conducting material, such as platinum, having a low affinity for oxygen and high corrosion resistance. The current density of the current flowing to the organ is precisely defined by defining the surface area of the jaws which engage the organ and transmit current to the organ. The remainder of the surface area adjacent to the defined surface which contacts the organ or body parts or fluids is coated with insulating material.

10 Claims, 28 Drawing Figures

CATHETER

REFERENCE TO RELATED APPLICATIONS

This application is a continuation-in-part of application Ser. No. 756,630 filed Jan. 4, 1977 to George J. Magovern, Frederick J. Shipko and George William Roland and assigned to CORATOMIC, Inc. now abandoned.

BACKGROUND OF THE INVENTION

This invention relates to the surgical art and has particular relationship to catheters for conducting electrical current to parts of the body. Specifically, catheters serve to conduct current to organs, such as the heart or the diaphragm, which are stimulated by electrical current. In the interest of relying here on concrete treatment of the invention to aid those skilled in the art to understand this invention, this application is on the whole confined to a catheter for a heart pacer. However, to the extent that this invention is applicable to parts of the body and organs other than the heart, such application is within the scope of this invention.

Typically, a catheter for a heart pacer includes a hollow closely-wound coil, typically of MP35N wire. MP35N is an alloy in weight percent of Ni35-Co35-Cr20-Mo10. The coil is encased in a jacket of silicone rubber. Where the heart is supplied from a pole of the supply through a single conductor with the opposite pole of the supply grounded, the cathether has at one end a plug which engages a socket or receptacle in the pacer. At the other end arcuate needles or like mechanisms for connection or suturing to the heart are provided. Where two conductors are used, like facilities are provided. The contraction of the heart muscle which the current from the catheter produces is dependent on the density of this current; i.e., on the magnitude of the current per unit area. The current density may be measured in amperes or milliamperes per square centimeter or square millimeter. The current density must exceed a predetermined threshold magnitude. Typically, the threshold current is 2 to 4 milliamperes per 10 square millimeter area at 5 volts and a 0.5 millisecond duration pulse. If threshold is too high, the muscle contraction does not take place. It is essential that the connection of the catheter to the heart be effective and reliable and of low resistance and be effected with a minimum of discomfort to the patient. It is also essential that the connection be such that the current density reliably exceeds the threshold current density. It is an object of this invention to provide a catheter which shall be capable of being so connected to the heart or other organ.

As a starting point of this invention, extensive work has been carried out with catheters having cooperative resiliently actuable hooks or jaws for connection to the heart muscle. Preliminary experiments had indicated that this catheter would operate satisfactorily. Such a catheter is shown in U.S. Pat. No. 4,011,875, Lehr, et al. A number of such catheters were implanted in dogs. It was found that these catheters operated erratically. A few operated satisfactorily over a relatively long time interval. The others supplied current of adequate density at the start, but the current fell off rapidly and in a relatively short time, a few days or a week, the necessary contraction of the heart muscle no longer took place.

It is an object of this invention to overcome the disadvantages of the above-described prior art and to provide a catheter for an implanted electrical generator which shall include resiliently actuable jaws for connection to the organ to be stimulated without major surgery such as open-heart surgery and without resulting discomfort or injury to the host and which shall reliably and for long time intervals conduct to the organ current of a density exceeding the required threshold current density.

SUMMARY OF THE INVENTION

This invention arises from the discovery of several factors which caused the above-described prior-art catheter to operate erratically. By examination of catheters as described above, it was discovered that blood and other body fluids had penetrated to the hollow electrical conductor. The blood and the fluids exert substantial pressure (about 50 or 60 millimeters of mercury) and will force themselves into the conductor through a very small opening in a seal. A portion of the current which was to be conducted to the heart was diverted or shunted by these fluids. It was also discovered that the jaws of the catheter, which were composed of titanium alloy, became oxydized, forming a thin oxide film, after a relatively short time of use, thus materially reducing the current flow to the heart muscle. The current density then became too low to contract the muscle reliably if at all. It was also discovered that the surface area of the jaws or clamp in direct or indirect electrical contact with the heart muscles varied for different implanted catheters because of differences in the heart structures and/or differences in the implantation or in the part of the heart which was clamped. It was realized that for the same total current, transmitted to the clamp, differences in the surface area of the jaws or clamp in electrical contact with the heart results in differences in current density. Where the surface area is so small that the current density exceeds the threshold magnitude, satisfactory operation is achieved. Where the surface area is larger so that the current density is marginal, the operation is sporadic. Where the surface area is so large that the current density is well below the threshold, the catheter fails to operate altogether.

In this invention there is provided a catheter including an electrical conductor having at one end the usual terminal for connection to an implanted generator and at the opposite end a clamp. The jaws of the clamp may be resilient. The resilient jaws may be normally closed and, in reliance upon their resilience, may be opened and reclosed in engagement with the heart muscle. Alternatively, the jaws may be normally open and may be provided with a toggle mechanism or linkage for closing them in engagement with the heart muscle. The conductor may be hollow and the clamp is provided with a mechanism operable remotely through the hollow conductor for selectively opening and closing its jaws.

In accordance with this invention, a seal is provided between the portion of the clamp which is contacted by the fluids of the body and the electrical conductor which effectively and reliably prevents the penetration of these fluids into the conductor. A cap or boot of a resiliently yieldable material, such as rubber, extends over the conductor. The boot has slots where it is penetrated by the legs of the clamp, intermediate the jaws and the junction of the clamp and the conductor. The effective seals are provided by adhesive at these slots. The adhesive is held securely by suture threads wound in notches, a notch on each leg of the clamp on the inside of the boot and a notch on each leg on the outside.

Also in accordance with this invention, the surface of the clamp along at least a portion of is length extending from the jaws inwardly (towards the pacer and away from the contemplated heart connection) is of a material which is electrically conducting, has a low affinity for oxygen, and is corrosion resistant. The clamp as a whole or the above-described portion of the clamp may be composed of this material or it may be plated by electroplating with the material. Platinum and other noble metals are suitable for this purpose. The material, particularly where the clamp is plated, may be one of the class consisting of:

platinum
iridium
palladium
rhenium
rhodium
osmium
ruthenium
gold

The alloy MP35N is also suitable for this purpose. With the surface of the clamp which engages the organ of the material described, the reduction of the current flowing to the muscle by reason of reaction of this surface with body fluids is prevented.

In addition, in accordance with this invention the area of the surface of the jaws of the clamp which are in contact with the muscle and through which the current flows to the muscle is precisely defined to maintain the current density at the desired magnitude exceeding the threshold. For this purpose the clamps are coated, except over a precisely defined surface area, with an insulating coating in the region where they come or may come directly or indirectly into contact with the muscle or with body fluids near the muscle. The uncoated area is the portion of the jaws which directly engages the muscle.

In the use of the catheter according to this invention with a heart pacer, a small incision, sufficient to implant the pacer, is made in the upper chest. With the aid of fluoroscope or other X-ray apparatus, the catheter with the clamp at the lead end is passed from the small incision through a vein, typically, to the right ventricle. To stiffen the catheter for this process, a stylet is inserted coaxial with the hollow conductor before it is passed through the vein. The stylet must be such as to permit bending of the stiffened catheter as it passes through the bends in the veins. The stylet is then removed and if the catheter is of the type requiring an external manipulator, the manipulator is passed through the hollow conductor. With the aid of the fluoroscope or X-ray apparatus, the manipulator is manipulated to engage the jaws of the clamp with tissue of the heart, typically the trabeculae carneae. The manipulator is then retracted and the catheter is connected to the pacer. The manipulator may be formed of a material which permits its use both to stiffen the catheter and also to manipulate the clamp.

The catheter according to this invention produces a highly effective connection to the heart muscles. If the catheter is of the type in which a flexible linear member is permanently connected to operate the clamp, the engagement with the heart is effected by operation of this member. The portion of the jaws of the clamp which are not coated with the insulator are in direct engagement with the tissue of the heart. Since the surface which is in engagement has no affinity for oxygen and resists corrosion, permanent, effective and reliable electrical contact is established between the tissue and the jaws. The layer of insulation precisely limits the area of contact so that the required current density is achieved.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which:

FIGS. 7(a), (b), (c) are plan views showing successive steps in the forming of the clamp;

FIG. 10 is a fragmental plan view of this end of the tine as seen in the direction of the arrow X of FIG. 9;

FIG. 13 is a fragmental view in end elevation of the jaw taken in the direction of the arrow XIII of FIG. 11;

DETAILED DESCRIPTION OF EMBODIMENT

Figures 1, 1A, 1B:
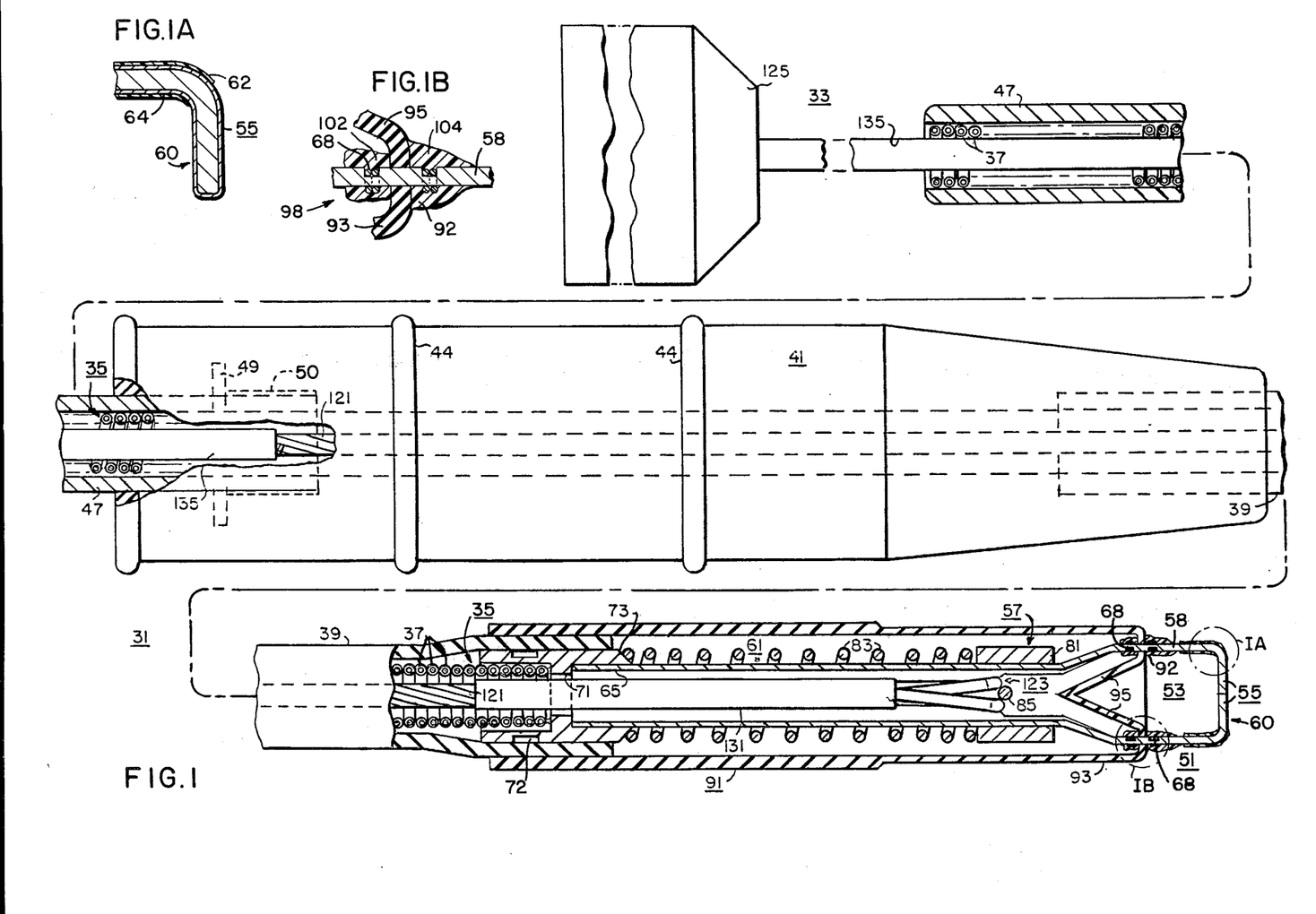
FIG. 1 is a view partly in longitudinal section and partly in side elevation showing a catheter and an external manipulator in accordance with this invention with the manipulator in the position which it assumes when first inserted into the hollow conductor of the catheter.
FIG. 1A is a fragmental view in section enlarged of the portion of a jaw of the clamp included in circle IA showing the plating and the insulation layer on the clamp.
FIG. 1B is a fragmental view in section enlarged of the portion of a leg of the clamp in circle IB showing the seal between the clamp and the boot which prevents the penetration of body fluids to the conductor.
Figure 2:
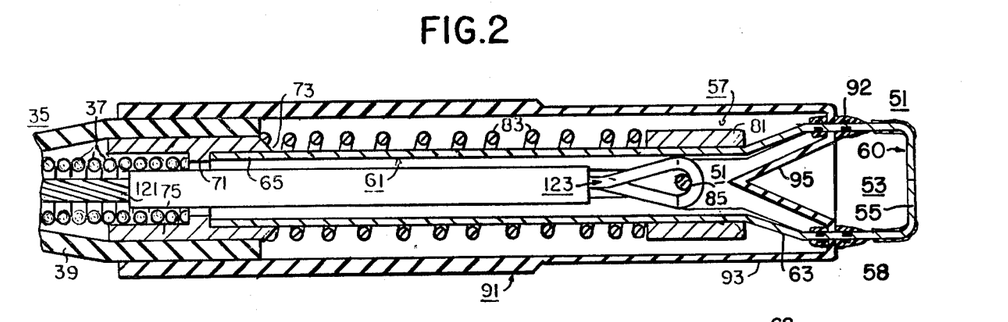
FIG. 2 is a fragmental view in section of the catheter and manipulator with the manipulator turned to a position in which it can manipulate the clamp.
Figures 3, 4, 5:
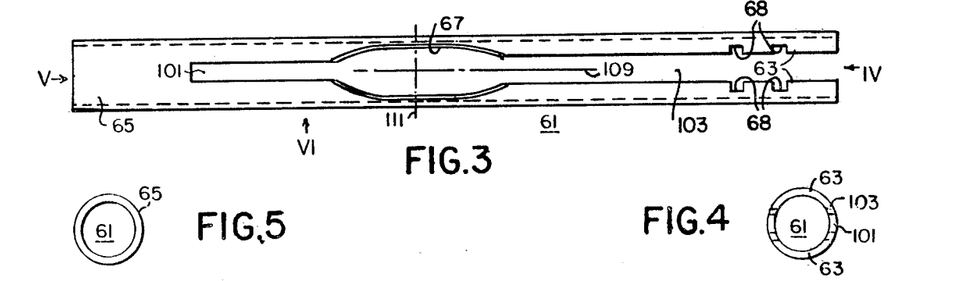
FIG. 3 is a plan view of the blank from which the clamp is formed.
FIGS. 4 and 5 are views in end elevation of the blank as seen in the directions of the arrows IV and V of FIG. 3, respectively.
Figure 6:
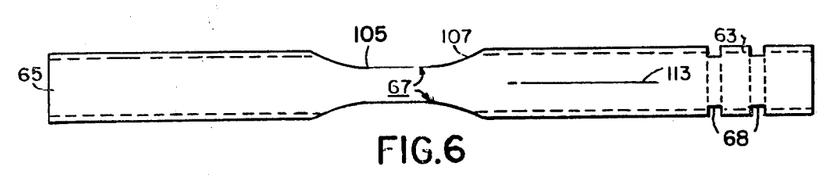
FIG. 6 is a view in side elevation of the blank as seen in the direction of the arrow VI of FIG. 3.

The apparatus shown in the drawings includes a catheter 31 and a manipulator 33. In FIGS. 1 and 2 the manipulator 33 is shown within the catheter in position to carry out its manipulating operation.

Figure 19:
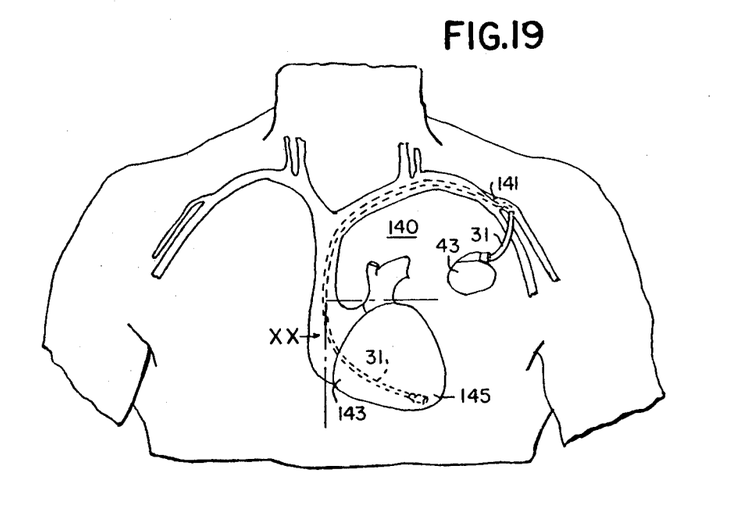
FIG. 19 is a diagrammatic view showing the manner in which the catheter according to this invention is implanted and connected to the heart.

The catheter 31 includes a hollow conductor 35 in the form of a closely-wound turns 37 typically composed of MP35N alloy. The conductor 35 is enclosed in a sheath 39 of silicone rubber of the type which is not rejected by the body. Near the inner end (the end connected to the pacer 43) a terminal 41 of hard rubber is molded about the conductor 35. The sheath 39 extends to the outer end of terminal 41 and is bonded to the terminal. The terminal 41 plugs into a receptacle (not shown, Purdy et al. U.S. Pat. No. 3,866,616) in the heart pacer 43 (FIG. 19). When the terminal is plugged in, the receptacle is sealed against penetration of body fluids by O-rings 44 on the terminal. The conductor 35 extends beyond the terminal 41 and is, at its inner end, ensheathed in a tubular terminal pin 47 which serves to connect to the electrical output of the pacer 43. The pin 47 extends into the terminal 41 and is welded to pin-anchoring washer 49 and to the conductor 35. A brazing shim 50 of platinum foil is wound about pin 47. The terminal 41 is molded about the sheath 39, the conductor 35, the outer end of the pin 47 and the anchoring washer 49. The anchoring washer 49 prevents the conductor 35 from being pulled out of the terminal.

A clamp assembly 51 extends from the opposite end (the outer end) of the catheter 31. This assembly 51 includes a clamp 53 having jaws 55 and a mechanism 57 for opening or closing the jaws 55. The jaws 55 include arms 58 generally in the length direction of the catheter from which fingers 60 extend at a well defined angle typically at right angles. The fingers 60 and the arms 58 and a portion of the clamp 53 inwardly of these parts has a plating 62 (FIG. 1A) of a metal, such as platinum, having a low affinity for oxygen and high corrosion resistance. Except over the fingers 60, this plating 62 and a portion of the clamp 53 inwardly of the fingers is covered by an insulating layer 64 typically of parylene-C, so that only the fingers 60 are transmitting current between the body tissue and the pacer. It has been found that parylene-C when deposited by vapor deposition forms a uniform coating even around sharp projections and sharp corners. Satisfactory coatings are produced by Union Carbide Corporation. Other insulating materials may also be used.

Figure 11:
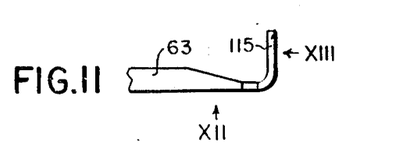
FIG. 11 is a fragmental view in side elevation of a jaw of the clamp formed from the tine shown in FIG. 8.
Figure 12:
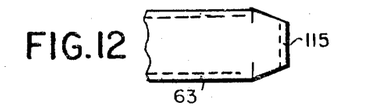
FIG. 12 is a fragmental plan view of the jaw taken in the direction of the arrow XII of FIG. 11.

The clamp is formed from a fork-shaped tubular blank 61 (FIGS. 3-6). The blank has tines 63 extending from a slotted stem 65. Between the stem 65 and their outer ends the tines 63 have attenuated half-oval portions 67. To form the fingers 60 the tines 63 are bent towards each other (FIGS. 11-13). Near its ends where the tines are to be bent to form fingers 60, but inwardly of the fingers, each tine 63 is provided with a pair of notches 68. The stem 65 serves as the stem for the clamp 53. The blank 61 is typically composed of the highly resilient titanium alloy Ti6A14V.

A coupling collar or stem 71 (FIGS. 7(a), (b), (c)) having a groove 72 (FIG. 1) intermediate its ends is welded to the stem 65 of the blank 61. The coupling stem 71 is tapered at the outer end. It has an opening extending from the taper 73 into which the stem 65 extends. The stem 65 is welded to the coupling stem 71 by laser welding at the outer end of the taper 73. At its inner end near the groove 72 the coupling stem 71 has an opening 75 into which the conductor 35 extends (FIGS. 2) to point outwardly of the groove 72. The conductor 35 is welded in the stem 71. The welding is effected by a laser beam which impinges on the outer surface of the stem 71 at the groove 72. The coupling stem 71 is typically composed of the platinum alloy Pt10Ir or other alloy which is readily welded to the titanium alloy Ti6A14V.

A ring 81 extends slideably over the attenuated portion 67 (FIG. 27a, b, c) of the tines 63, which form the jaws 55, and over the adjacent outer portion of the stem 65. A spring 83 (FIG. 1,2) extends from the taper 73 of the coupling stem or collar 71 at one end to the ring 81 at the other. A pin 85 extends through the ring 81 and is welded to it. The ring 81 is typically composed of the alloy Pt10Ir and the spring 83 and pin 85 of MP35N.

The coupling stem 71 is secured in the outer rim of the sheath 39. So that the stem 71 is held securely, the outer diameter of the stem 71 is greater than the inner diameter of the sheath 39. The force of the spring 83 is exerted between the stem 71 and the ring 81 and normally urges the ring outwardly so that it slides along the attenuated portion 67 of the jaws 55 to close the jaws. The jaws 55 may be opened by compressing and retracting the spring 83.

A rubber cap or boot 91 extends over the spring 83, the ring 81 and the other parts. The purpose of this cap 91 is to prevent the penetration of body fluids into the catheter. The cap 91 is bonded to the sheath 39 at one end. The cap 91 is reduced in thickness at the end 93 near the clamp 53 and terminates in a reentrant conical tip 95 (FIG. 1(c)) at this end still further reduced in thickness. The jaws 55 pass through slots 96 on the end of the cap 91 and are sealed tightly at seals 98 (FIG. 1B) in these slots with silicone rubber adhesive 92. The seals 98 are formed, in accordance with this invention, to prevent any penetration of body fluids, into the boot 91. Several loops of thread 100 are wrapped around each notch 68 in the tines 63. Typically the thread is surgical polyester braided fiber of 0.002 inch thickness. The clamp 51 penetrates the slots 96 in the boot 91 with a notch 68 in each leg on the outside of the boot and a notch in each on the inside. Silicone rubber adhesive is applied about each slot 96 so as to seal the junctions of the boot and the legs of the clamp. The adhesive 102 is applied to the inside of the boot 91 first by displacing the rubber at each slot 96. Then the adhesive 104 is applied to the outside. The thread 100 anchors the adhesive in each case. The attenuated portion of the cap 91 and the conical tip 95 enable the casing to yield without restricting the movement of the jaws as the jaws 55 are opened and closed. Typically, the clamp 51 is bent so that the fingers 60 open 0.100 inch before the clamp is sealed in the boot 91 and 0.080 to 0.090 after the clamp is sealed.

Typically, the catheter 31 has a length of about 24 inches. The inside diameter of conductor 35 is typically 0.040" and its outside diameter 0.060". The conductor 35 is accordingly typically formed of 0.010 wire. The inside diameter of the sheath 39 is typically 0.062' and the outside diameter, 0.095".

The blank 61 (FIGS. 3–6) is formed of tubing typically of 0.046" inside diameter and 0.062 ± 0.0005" outside diameter. Other typical dimensions of the blank 61 are as follows:

length = 0.660"
distance from outer end of tines to inner end of slot 101 = 0.560"
width of slot 103 between tines 63 = 0.025"
length of slot cut to form tines 63 = 0.360"
width of slot 101 = 0.015"
length of straight section 105 of attenuated portion 67 (FIG. 6) = 0.056"
radius of end 107 of attenuated portion 67 = 0.088"
distance of center of straight portion 105 (center of attenuated portion 67) from inner end of stem 65 = 0.267"
distance of inner end of tines to inner boundary of notches 68 = 0.120L"
width of each notch 68 = 0.010"
distance between notches = 0.025"
depth of each notch = 0.010"

In forming the blank 61, the 0.025" width slot 103 is first cut to a length of 0.360" from one end of a tube of the above inner diameter and outer diameter. The 0.360" slot is centered about the axial plane 109 of the tube. The notches 68 are formed in the tines 63 bounding this slot 103. Coextensive with the slot 103, a narrower slot of 0.015" width is cut to a distance of 0.560" from the same end of the tube. The attenuated portion 67 is then formed. This portion is centered about an axis 111, 0.360" from the end of the tube. The attenuated portion 67 is centered about an axial plane 113 perpendicular to plane 109. The ring 81 must be closely dimensioned to slide along the stem 65 and attenuated portion 67. The inner diameter of the ring 81 is 0.059+0.002−000" and its outer diameter 0.090". The edges of the ring 81 at both ends are rounded.

Figure 7:
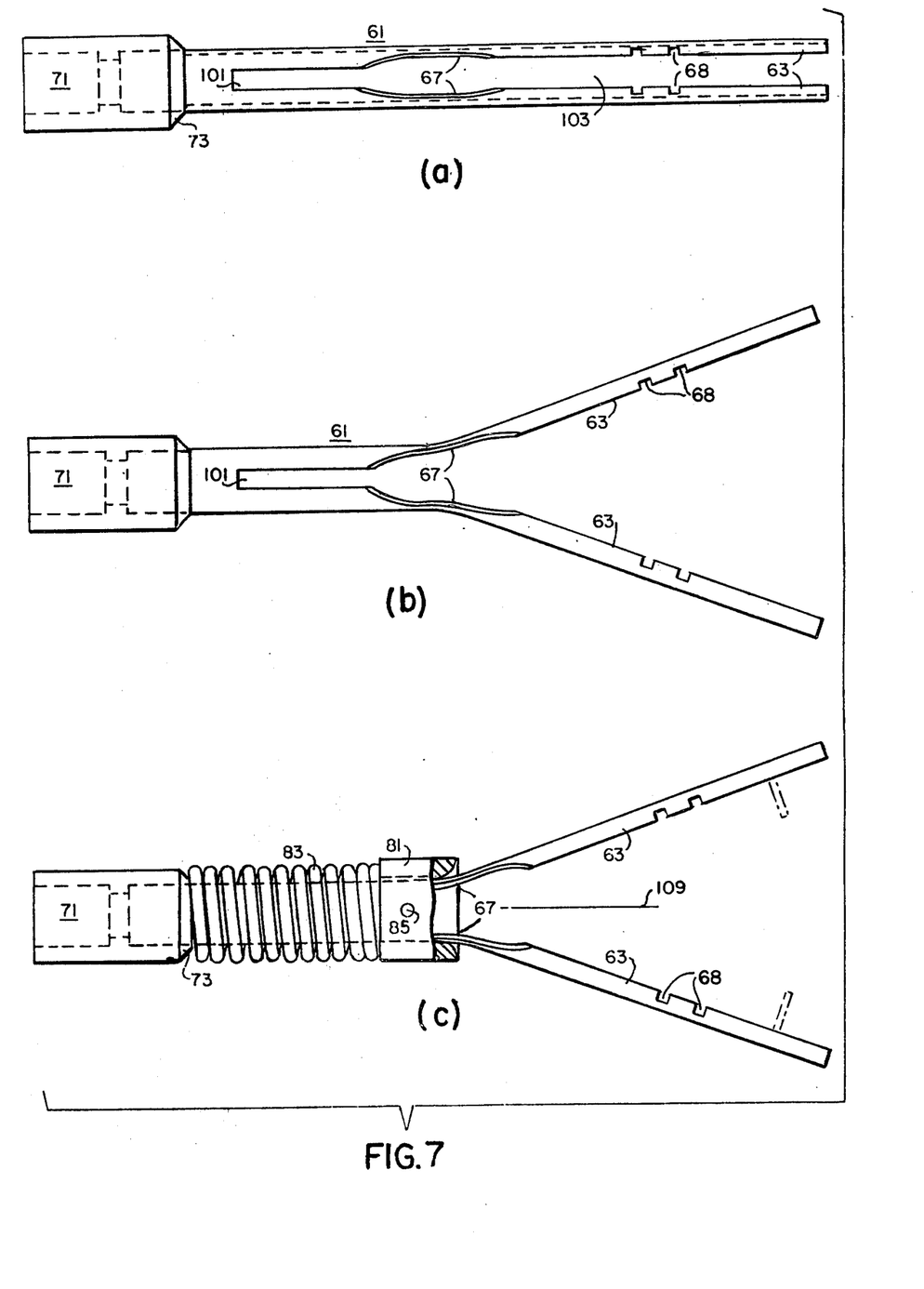

In forming the clamping assembly the stem 65 of the blank 61 is first inserted into the coupling stem or collar 71 (FIG. 7 at (a)). The stem 65 is welded to the coupling stem 71 at the taper 73. The tines 63 of the blank are then bent outwardly as shown in FIG. 7 at (b). The bending of each case is about an axis 0.295" from the inner end of the stem 65 or 0.380" from the inner end of the coupling stem or collar 71. For the material and dimensions disclosed here, the tines 63 are bent at an angle typically of 17° to the axial plane 109. The spring 83 is then passed over the tines 63, which are compressed, and the stem 65 and welded at its inner end to the taper 73 of the coupling stem 71 (FIG. 7 at (c)). The ring 81 with the pin 85 welded at both surfaces of the ring 81 is then passed over the tines 63, which are compressed, and engaged with the spring 83. The spring 83 is welded to the inner end of ring 81. With the spring 83 compressed, the tines 63 are separated as shown in FIG. 7 at (c). With the spring 83 relaxed, the tines 63 are forced inwardly by the ring 81.

Figure 8:
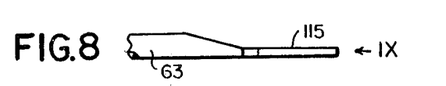
FIG. 8 is a fragmental view of the end of the tine shown in FIG. 7(c) prior to the formation of a jaw of the clamp.
Figure 9:
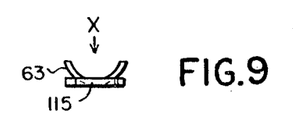
FIG. 9 is a fragmental view in end elevation of this end of the tine as seen in the direction of arrow IX of FIG. 8.

Attenuated tip 115, typically of 0.055" length are then cut in the ends of the tines (FIGS. 8, 9, 10). The attenuated tips 115 are then bent inwardly at right angles to the tines 63 to form the fingers 60. The radius of this bend is about 0.010" (FIGS. 11, 12, 13).

Figures 1C, 13A, 22, 23, 24:
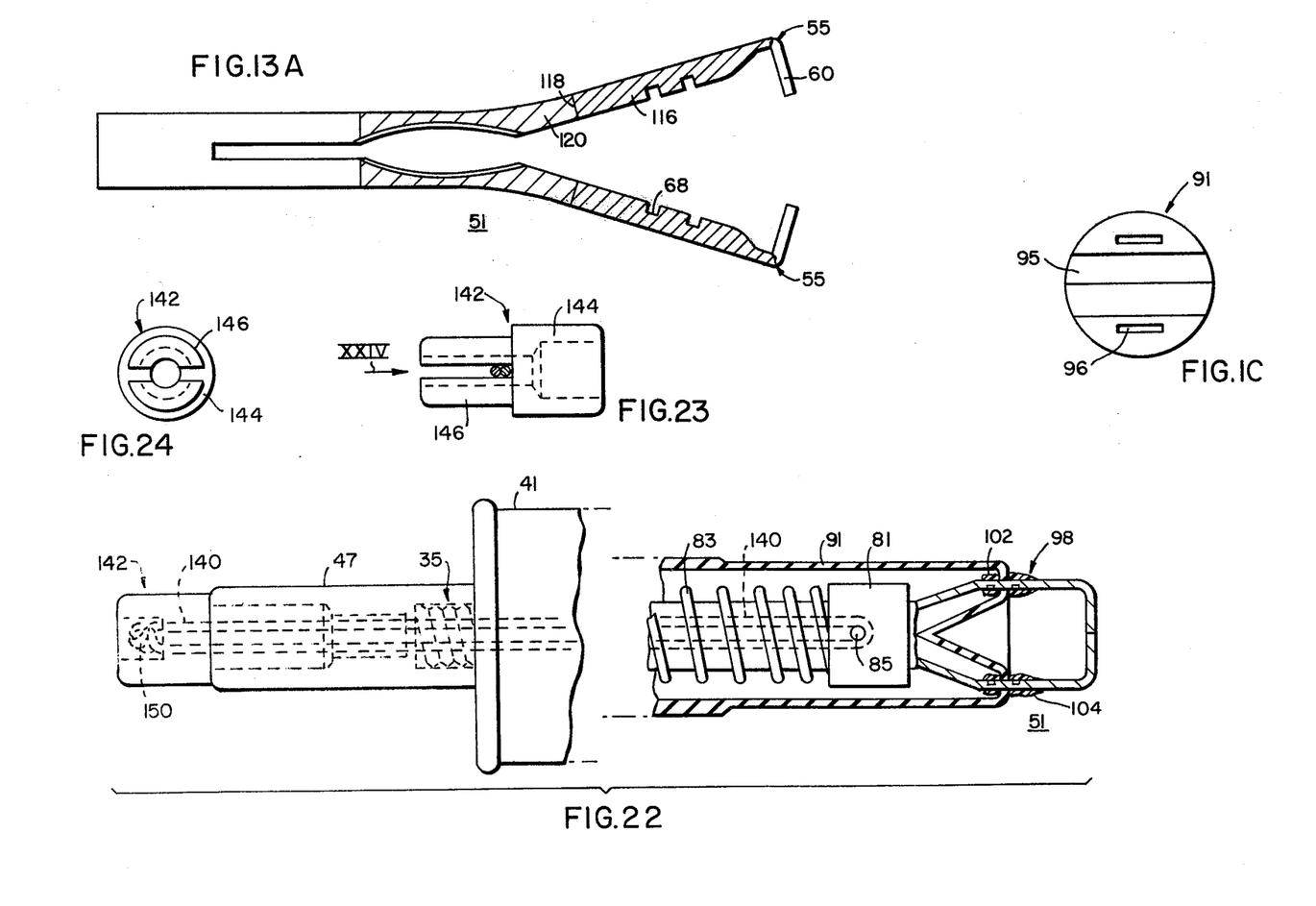
FIG. 1C is a view in end elevation of the boot or cap which extends over the inner end of the catheter.
FIG. 13A is a view in side elevation of the clamp showing the regions of the clamp over which the plating and coating of insulation are applied during the fabrication of the clamp.
FIG. 22 is a view partly in side elevation and partly in section of a catheter in accordance with a modification of this invention in which a permanent flexible linear member is provided for manipulating the jaws of the clamp.
FIG. 23 is a view in side elevation of the pin cap of the catheter shown in FIG. 2 in which the linear member is secured.
FIG. 24 is a view in end elevation as seen in direction of arrow XXIV of this pin cap.

After the clamp 51 is formed and assembled, it is plated with the corrosion-resistant-low-oxygen affinity plating 62. Then it is coated with the electrically insulating coating 64, typically parylene. The parylene coating is about 0.001" thick. Then the parylene is removed from the fingers 60. FIG. 13A is a diagrammatic view of the clamp 51, presented purely for the purpose of explaining this invention, showing shaded the areas which are plated and coated. The darker area 116 extending from the inner ends of the fingers 60 to the lines 118 is both plated and coated. The lighter area 120 is only coated. The actual plating and coating takes place with the ring 81 and spring 83 on the clamp 51. The plating and coating takes place at this stage of the operation after the forming operation to preclude the plating and/or coating being cracked by the forming.

As described above, the collar 71 and the spring 83 are mounted on blank 61 before it is formed into clamp 51. The blank 61 may also be formed into a clamp before the collar 71 and spring 83 are mounted on the blank. This procedure may be advantageous to facilitate the plating and coating operations.

Figure 14:
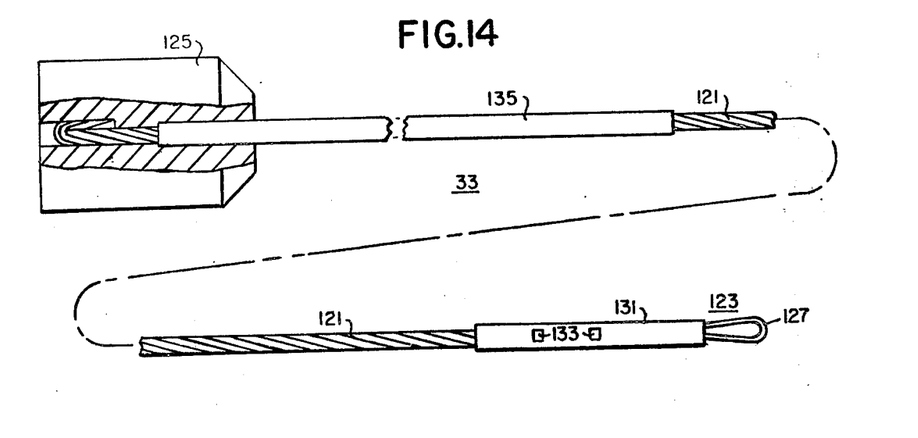
FIG. 14 is a view in side elevation of the manipulator for manipulating the clamp.
Figure 15:
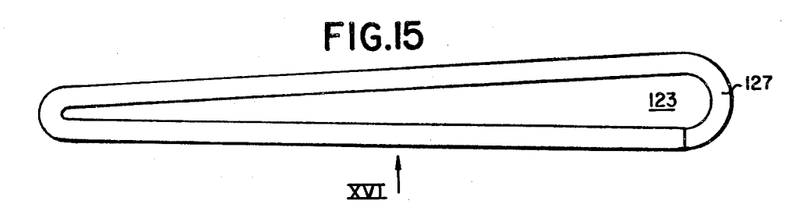
FIG. 15 is a plan view of the mechanism at the end of the manipulator for manipulating the clamp.
Figure 16:
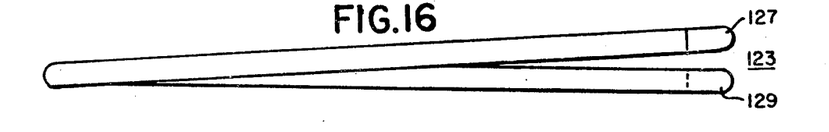
FIG. 16 is a view in side elevation of this mechanism taken in the direction of the arrow XVI.
Figure 17:
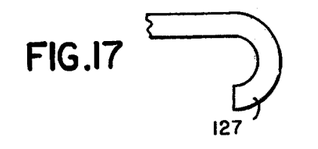
FIGS. 17 and 18 are fragmental views in side elevation of the hooks of this mechanism.
Figure 18:
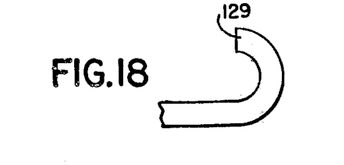

The manipulator 33 includes a cable 121 (FIG. 14). Typically, the cable is composed of strands of stainless steel wire. Typically, there are seven strands of 0.005" diameter forming a cable of 0.018" diameter. The cable 121 is typically about 25.80 ± 0.25" long. At one end of the cable 121 there is a manipulating mechanism 123 (FIGS. 15–18) and at the opposite end there is a knob 125 for manipulating the manipulator 33.

The mechanism 123 is formed from a wire typically of stainless steel about 0.010" in radius. At each end of the wire a hook 127 and 129 is formed. Each hook 127 and 129 is of semi-circular shape 0.010' in inner radius. The hooks 127 and 129 are formed oppositely. The wire is folded over at the center and skewed so that the hooks 127 and 129 are displaced. The mechanism 123 is held on the end of the cable 121 by a sleeve 131 of stainless steel, typically 0.032' outer diameter and 0.022" inner diameter. The mechanism 123 is welded to the cable by laser welding through slots 133 in the sleeve. Typically, the sleeve 131 has a length of 0.40" and the mechanism 123 extends out of the sleeve a distance of 0.10".

At the end near the knob 125 the cable 121 has a sleeve 135 of the same material and diameter as the sleeve 131, but typically 1.20" in length. The knob 125 is typically composed of high-density polypropylene and has an axial opening. The cable 121 extends beyond the sleeve 135 and is folded over at the end. The sleeve 135 and cable 121 extend into the opening and are secured therein. The length of the manipulator 33 from the inner end of the knob 125 to the outer end of the mechanism 123 is typically 26 ± 0.25". The sleeve 135 facilitates the thrusting into the conductor 37 and turning of the manipulator 33.

Figure 20:
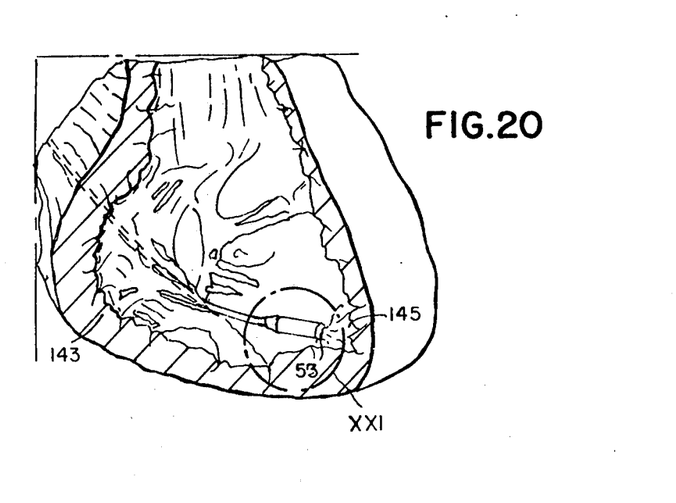
FIG. 20 is a fragmental view, enlarged, of the portion of FIG. 19 in the right angle XX.
Figure 21:
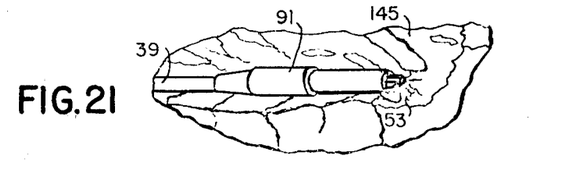
FIG. 21 is a fragmental view, enlarged, of the portion of FIG. 20 in the circle XXI.

In the use of the apparatus according to this invention, a small incision is made in the chest 140 (FIG. 19) where the pacer 43 is to be implanted. The catheter 31, stiffened by a stylet (not shown), is passed through a vein 141 from a position near the incision to a position in the right ventricle 143 where the clamp 53 is near the trabeculae carneae 145 (FIGS. 20, 21). The clamp 53 is closed by the ring 81. The stylet is then removed and with the aid of the knob 125, the manipulator 33 is thrust through the catheter 31 to a position in which the mechanism 123 is within the ring 81 with the hooks 127 and 129 on opposite sides of the pin 85 as shown in FIG. 1. With the aid of the knob 125, the manipulator 33 is turned at right angles about its axis so that the hooks 127 and 129 are interlaced with the pin 85 as shown in FIG. 2. The manipulator 33 is then retracted a short distance by use of the knob 125 pulling the pin 85 inwardly and compressing and retracting the spring 83. The jaws 55 of the clamp 53 spring open and the fingers 60 are engaged with the trabeculae carneae. The manipulator 33 is then released so that the spring is released and the fingers 60 are locked in engagement with the trabeculae carneae. The manipulator 33 is then turned back at right angles and removed and the catheter 31 is connected to the pacer 43 and the operation proceeds to completion. The steps following the incision are carried out with the aid of fluoroscope or other X-ray apparatus.

The embodiment of this invention shown in FIGS. 22, 23, 24 has a permanent facility for remotely manipulating the clamp 51 in place of the manipulator 33. The clamp is manipulated by a string 140 which is looped around the pin 85 and extends through the hollow conductor 35 to the end of the terminal pin 47. The string 140 is surgical polyester braided fiber 0.010" in diameter. The terminal pin 47 has an opening in its inner end into which a pin cap 142 (FIGS. 23 and 24) is inserted. The pin cap 142 has a head 144 from which a slotted stem 146 extends. The parts or legs of the stem 146 are spread so that the cap 142 fits tightly in the end of the pin 47. The cap 142 has an axial opening through which the ends of the string 140 are passed. The ends of the string 140 are knotted at 150, deposited in the opening in cap 142 and secured therein by epoxy adhesive. When the clamp is to be manipulated, the cap 142 is removed from the pin 47 and pulled away from the end of the pin 47. The jaws 55 are then opened. The cap 142 is then retracted so that the fingers 60 engage the tissue of the heart. Then the cap is inserted in the pin 47. The cap may be composed of titanium alloy.

Several catheters, in accordance with this invention, as described in FIGS. 22 through 24, have been implanted in dogs and have yielded highly satisfactory operation. It was found that satisfactory muscle contraction takes place for acute current density of 0.1 to 0.2 milliamperes per 10 mm$^2$ for a 0.5 millisecond duration.

While preferred embodiments of this invention are disclosed herein, many modifications thereof are feasible. This invention is not to be restricted except insofar as is necessitated by the prior art.

We claim:

1. A catheter, for use in supplying current to an organ of a body, said catheter including an electrical conductor, a clamp, connected in electrically conducting relationship with said conductor near the end of said conductor that is to be nearest said organ, said clamp having resilient jaws to be clamped to said ogan in electrically conducting relationship therewith, means, connected to said clamp for opening and closing said jaws in reliance upon their resilience, means composed of resiliently yieldable material interposed between said clamp and said conductor to prevent the penetration to said conductor of body fluids from the region where said clamp is clamped to said organ, said clamp passing through said fluid-penetration-preventing means, and means for sealing the junction between said clamp and said fluid-penetration-preventing means where said clamp passes through said fluid-penetration-preventing means.

2. The catheter of claim 1 wherein the surface of at least the portion of the clamp, including the surface of the jaws is composed of a material which is electrically conducting, has a low affinity for oxygen and is corrosion resistant.

3. The catheter of claim 2 wherein the surface of at least the portion of the clamp which has a low affinity for oxygen and is corrosion resistant is coated with a non-conducting coating except for a defined predetermined surface area of the jaws, substantially the whole of said area to be in electrically conducting engagement with the organ, whereby the current density of the current transmitted to the organ is defined.

4. The catheter of claim 1 wherein the surface of the jaws which is to engage the organ in electrically conducting relationship and through which the current is to flow to the organ is of defined predetermined surface area.

5. The catheter of claim 1 wherein the clamp includes arms from each of which the jaws extend, each said jaw including at its end a finger extending at a sharp angle from the adjacent portion of said jaw, the fingers engaging the organ in electrically conducting relationship, substantially the whole surface of each finger being composed of a material which is electrically conducting, has a low affinity for oxygen and is corrosion resistant, and the portion of the clamp near said fingers being coated with electrically non-conducting material, so that electrical current is conducted only through said fingers.

6. The catheter of claim 1 wherein the end of the electrical condutor that is to be nearest the organ has a cap of flexible material, the clamp extending through the end of the cap that is to be nearest the organ, the joint between the cap and the clamp being sealed against penetration of body fluids to said conductor.

7. The catheter of claim 1 wherein the electrical conductor is hollow and the clamp includes arms from which the jaws extend, said clamp being formed to exert a resilient force tending to open said jaws, a ring encircling said arms and being slideable along said jaws, resilient means uging said ring along said legs towards said jaws, said ring exerting a force counteracting said resilient force to maintain said jaws normally closed, and a flexible linear member connected to said ring and, extending through said hollow conductor to its remote end, for retracting said ring to open said jaws for engagement with the organ.

8. The catheter of claim 7 wherein a pin extends transversely through the ring and the flexible linear member engages the pin.

9. A catheter, for use in supplying current to an organ of a body, said catheter including an electrical conductor, a clamp connected, in electrically conducting relationshp with said conductor, to the end of said conductor that is to be nearest said organ, said clamp having jaws to be clamped to said organ in electrically conducting relationship therewith and a leg extending from each of said jaws, a ring encircling said legs, resilient means in engagement with said ring urging said ring towards said jaws to maintain said jaws closed, and means, remotely actuable for retracting said ring in the direction away from said jaws against the action of said resilient means, to permit said jaws to open.

10. A catheter, for use in supplying current to an organ of a body, said catheter including an electrical conductor, resilient clamp means, means connecting said clamp means in electrically conducting relationship with said conductor near the end of said conductor that is to be nearest said organ, said clamp means having jaws to be clamped to said organ and to engage said organ in electrically conducting relationship over a limited surface area of said jaws, at least the potions of said jaws defined by said limited area, being composed at least on their surfaces of a material which is electrically conducting, has a low affinity for oxygen and is corrosion resistant, means, connected to said clamp means, for opening and closing said jaws in reliance upon the resiliance of said clamp means, and means, interposed between said clamp means and said conductor and said jaw-opening and closing means, resiliently operable with said jaws as they are opened and closed, preventing the penetration of body fluid to said jaw-opening-and-closing means and said conductor.

* * * * *